(12) United States Patent
Traina (10) Patent No.: US 12,064,583 B1
(45) Date of Patent: Aug. 20, 2024

(54) CONNECTOR ASSEMBLY

(71) Applicant: Becton, Dickinson and Company, Franklin Lakes, NJ (US)

(72) Inventor: Zachary Jarrod Traina, Denville, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/567,539

(22) PCT Filed: Jun. 7, 2022

(86) PCT No.: PCT/US2022/032418
§ 371 (c)(1),
(2) Date: Dec. 6, 2023

(87) PCT Pub. No.: WO2022/261034
PCT Pub. Date: Dec. 15, 2022

Related U.S. Application Data

(60) Provisional application No. 63/197,769, filed on Jun. 7, 2021.

(51) Int. Cl.
*A61M 39/10* (2006.01)
(52) U.S. Cl.
CPC ......... *A61M 39/10* (2013.01); *A61M 2205/50* (2013.01)
(58) Field of Classification Search
CPC  H01R 13/5219; H01R 2201/12; H01R 24/58; H01R 43/20; A61N 1/3752; A61M 39/10; A61M 2205/50
See application file for complete search history.

(56) References Cited

U.S. PATENT DOCUMENTS

| 7,654,843 | B2 * | 2/2010 | Olson | A61N 1/3752 |
| | | | | 439/248 |
| 7,717,754 | B2 | 5/2010 | Ries et al. | |
| 8,167,660 | B2 * | 5/2012 | Dilmaghanian | H01R 24/58 |
| | | | | 439/669 |
| 9,750,926 | B2 | 9/2017 | Lopez et al. | |
| 11,052,259 | B2 | 7/2021 | Stinauer et al. | |
| 2016/0015957 | A1 * | 1/2016 | Tieck | A61M 5/1456 |
| | | | | 604/533 |

FOREIGN PATENT DOCUMENTS

WO    2020163297 A1    8/2020

* cited by examiner

*Primary Examiner* — Brandy S Lee
(74) *Attorney, Agent, or Firm* — The Webb Law Firm (57) ABSTRACT

A connector assembly may include an inner housing and an outer housing surrounding the inner housing. The inner housing may include a fluid flow path extending between a proximal port and a distal port. An exterior surface of the inner housing may include a first electrically conductive exterior surface and a second electrically conductive exterior surface. An interior surface of the outer housing may include a first electrically conductive interior surface and a second electrically conductive interior surface. The outer housing may be configured to move radially and rotationally relative to the inner housing. A processer may determine, based on whether the electrically conductive exterior surfaces contact the exterior electrically conductive interior surfaces, radial data associated with a radial position of the outer housing relative to the inner housing and rotational data associated with a rotational position of the outer housing relative to the inner housing.

19 Claims, 8 Drawing Sheets

CONNECTOR ASSEMBLY

CROSS-REFERENCE TO RELATED APPLICATIONS

This application is the United States national phase of International Application No. PCT/US2022/032418 filed Jun. 7, 2022, and claims priority to U.S. Provisional Application Ser. No. 63/197,769, entitled "Connector Assembly", filed Jun. 7, 2021, the entire disclosures of which are hereby incorporated by reference in their entirety.

BACKGROUND

A needleless connector may be scrubbed with a disinfectant to disinfect the needleless connector. However, there is no existing mechanism for detecting disinfection of a needleless connector.

Further, identification of disposable medical devices is commonly performed with radio-frequency identification (RFID) tagging. Although robust and cost effective in higher volumes, RFID tagging uses significant operating power and increases cost, weight, and size of disposable medical devices, which may not be feasible for use with needleless connectors. RFID may also place limits on geometry and an orientation of a disposable medical device relative to a sensing device, which again, may not be feasible for use with needleless connectors.

SUMMARY

According to some non-limiting embodiments or aspects, provided is a connector assembly including an inner housing and an outer housing surrounding the inner housing. The inner housing may include a fluid flow path extending between a proximal port and a distal port. An exterior surface of the inner housing may include a first electrically conductive exterior surface and a second electrically conductive exterior surface. An interior surface of the outer housing may include a first electrically conductive interior surface and a second electrically conductive interior surface. The outer housing may be configured to move radially relative to the inner housing between a first radial position in which the first electrically conductive exterior surface is spaced apart from the first electrically conductive interior surface and a second radial position in which the first electrically conductive exterior surface is in electrical contact with the first electrically conductive interior surface. The outer housing may be configured to move rotationally relative to the inner housing between a first rotational position in which the second electrically conductive exterior surface is spaced apart from the second electrically conductive interior surface and a second rotational position in which the second electrically conductive exterior surface is in electrical contact with the second electrically conductive interior surface. A processor may be programmed and/or configured to: determine, based on whether the first electrically conductive exterior surface is in electrical contact with the first electrically conductive interior surface, radial data associated with a radial position of the outer housing relative to the inner housing; and determine, based on whether the second electrically conductive exterior surface is in electrical contact with the second electrically conductive interior surface, rotational data associated with a rotational position of the outer housing relative to the inner housing. Wireless communication circuitry may be configured to wirelessly communicate the radial data and the rotational data to an external computing device. A system may include the connector assembly and the external computing device.

Further non-limiting embodiments or aspects are set forth in the following numbered clauses:

Clause 1. A connector assembly, comprising: an inner housing including a fluid flow path extending between a proximal port and a distal port, wherein an exterior surface of the inner housing includes a first electrically conductive exterior surface and a second electrically conductive exterior surface; an outer housing surrounding the inner housing, wherein an interior surface of the outer housing includes a first electrically conductive interior surface and a second electrically conductive interior surface, wherein the outer housing is configured to move radially relative to the inner housing between a first radial position in which the first electrically conductive exterior surface is spaced apart from the first electrically conductive interior surface and a second radial position in which the first electrically conductive exterior surface is in electrical contact with the first electrically conductive interior surface, wherein the outer housing is configured to move rotationally relative to the inner housing between a first rotational position in which the second electrically conductive exterior surface is spaced apart from the second electrically conductive interior surface and a second rotational position in which the second electrically conductive exterior surface is in electrical contact with the second electrically conductive interior surface; at least one processor programmed and/or configured to: determine, based on whether the first electrically conductive exterior surface is in electrical contact with the first electrically conductive interior surface, radial data associated with a radial position of the outer housing relative to the inner housing; and determine, based on whether the second electrically conductive exterior surface is in electrical contact with the second electrically conductive interior surface, rotational data associated with a rotational position of the outer housing relative to the inner housing; and wireless communication circuitry configured to wirelessly communicate the radial data and the rotational data to an external computing device.

Clause 2. The connector assembly of clause 1, further comprising: a first electrical contact connected to the exterior surface of the inner housing; a second electrical contact connected to the interior surface of the outer housing, wherein the outer housing is configured to move axially relative to the inner housing between a first axial position and a second axial position, wherein a relative position between the first electrical contact and the second electrical contact changes as the outer housing moves between the first axial position and the second axial position, wherein the at least one processor is further programmed and/or configured to determine, based on the relative position between the first electrical contact and the second electrical contact, axial data associated with an axial position of the outer housing relative to the inner housing, and wherein the wireless communication circuitry is configured to wirelessly communicate the axial data to the external computing device.

Clause 3. The connector assembly of any of clauses 1 and 2, further comprising: a spring connected between the inner housing and the outer housing, wherein the spring is configured to transition between a resting state and a compressed or stretched state, wherein the spring is configured to be in the resting state when the outer housing is in the first axial position, wherein the spring is configured to be in the compressed or stretched state when the outer housing is in the second axial position, and wherein the spring causes the outer housing to return to the first axial position in response to a removal of an axial force holding the outer housing in the second axial position.

Clause 4. The connector assembly of any of clauses 1-3, further comprising: a printed circuit board assembly connected to the inner housing or the outer housing, such as an interior surface of the outer housing, wherein the printed circuit board assembly includes the at least one processor, the wireless communication circuitry, and the second electrical contact, wherein the printed circuit board assembly is electrically connected to each of the first electrically conductive interior surface and the second electrically conductive interior surface.

Clause 5. The connector assembly of any of clauses 1-4, wherein the second electrical contact includes a plurality of discrete electrical contacts spaced apart from each other, and wherein the first electrical contact is configured to selectively engage the plurality of discrete electrical contacts as the outer housing moves axially relative to the inner housing between the first axial position and the second axial position.

Clause 6. The connector assembly of any of clauses 1-5, wherein the second electrical contact includes a continuous resistive element, wherein the first electrical contact is configured to engage and move along a length of the continuous resistive element as the outer housing moves axially relative to the inner housing between the first axial position and the second axial position.

Clause 7. The connector assembly of any of clauses 1-6, wherein the radial data includes at least one of the following parameters: a number of times that the first electrically conductive exterior surface is in electrical contact with the first electrically conductive interior surface, a duration that the first electrically conductive exterior surface is in electrical contact with the first electrically conductive interior surface, or any combination thereof.

Clause 8. The connector assembly of any of clauses 1-7, wherein the rotational data includes at least one of the following parameters: a number of times the second electrically conductive exterior surface is in electrical contact with the second electrically conductive interior surface, a duration that the second electrically conductive exterior surface is in electrical contact with the first electrically conductive interior surface, or any combination thereof.

Clause 9. The connector assembly of any of clauses 1-8, wherein the axial data includes at least one of the following parameters: an amount of axial displacement of the outer housing relative to the inner housing from the first axial position toward the second axial position, a number of axial displacements of the outer housing relative to the inner housing from the first axial position toward the second axial position, a duration of an axial displacement of the outer housing relative to the inner housing from the first axial position toward the second axial position, a rate/speed of displacement, or any combination thereof.

Clause 10. The connector assembly of any of clauses 1-9, wherein the at least one processor is further programmed and/or configured to determine, based on the radial data and the rotational data, a disinfection event associated with the proximal port of the inner housing.

Clause 11. The connector assembly of any of clauses 1-10, wherein the at least one processor is further programmed and/or configured to determine, based on the axial data, a type of a medical device connected to the distal port of the inner housing.

Clause 12. The connector assembly of any of clauses 1-11, wherein the outer housing extends between a proximal end and a distal end, wherein the proximal end and the distal end of the outer housing are located between the proximal port and the distal port of the inner housing, wherein the printed circuit board assembly further includes a battery and user input device, and wherein the user input device extends through an opening in the outer housing between the proximal end and the distal end of the outer housing, alternatively, the user input device may be integral to the outer housing.

Clause 13. The connector assembly of any of clauses 1-12, wherein the communication circuitry is configured to establish communication with the external computing device in response to a predetermined user input to the user input device.

Clause 14. The connector assembly of any of clauses 1-13, wherein the connector assembly further includes a sealing ring between the proximal end of the outer housing and the proximal port of the inner housing.

Clause 15. A system, comprising: a connector assembly including: an inner housing including a fluid flow path extending between a proximal port and a distal port, wherein an exterior surface of the inner housing includes a first electrically conductive exterior surface and a second electrically conductive exterior surface; an outer housing surrounding the inner housing, wherein an interior surface of the outer housing includes a first electrically conductive interior surface and a second electrically conductive interior surface, wherein the outer housing is configured to move radially relative to the inner housing between a first radial position in which the first electrically conductive exterior surface is spaced apart from the first electrically conductive interior surface and a second radial position in which the first electrically conductive exterior surface is in electrical contact with the first electrically conductive interior surface, wherein the outer housing is configured to move rotationally relative to the inner housing between a first rotational position in which the second electrically conductive exterior surface is spaced apart from the second electrically conductive interior surface and a second rotational position in which the second electrically conductive exterior surface is in electrical contact with the second electrically conductive interior surface; at least one processor programmed and/or configured to: determine, based on whether the first electrically conductive exterior surface is in electrical contact with the first electrically conductive interior surface, radial data associated with a radial position of the outer housing relative to the inner housing; and determine, based on whether the second electrically conductive exterior surface is in electrical contact with the second electrically conductive interior surface, rotational data associated with a rotational position of the outer housing relative to the inner housing; and wireless communication circuitry configured to wirelessly communicate the radial data and the rotational data to an external computing device; and a computing system including one or more processors programmed and/or configured to determine, based on the radial data and the rotational data, a disinfection event associated with the distal port of the inner housing.

Clause 16. The system of clause 15, wherein the connector assembly further includes: a first electrical contact connected to the exterior surface of the inner housing; a second electrical contact connected to the interior surface of the outer housing, wherein the outer housing is configured to move axially relative to the inner housing between a first axial position and a second axial position, wherein a relative position between the first electrical contact and the second electrical contact changes as the outer housing moves between the first axial position and the second axial position, wherein the at least one processor is further programmed and/or configured to determine, based on the relative position between the first electrical contact and the second electrical contact, axial data associated with an axial position of the outer housing relative to the inner housing, wherein the wireless communication circuitry is configured to wirelessly communicate the axial data to the external computing device, and wherein the one or more processors are further programmed and/or configured to determine, based on the axial data, a type of a medical device connected to the distal port of the inner housing. Optionally, the at least one processor may locally make the determination on whether the unit is being scrubbed and/or what device may be attached, this may be provided by immediate feedback through a light source LED.

Clause 17. The system of any of clauses 15 and 16, wherein the radial data includes at least one of the following parameters: a number of times that the first electrically conductive exterior surface is in electrical contact with the first electrically conductive interior surface, a duration that the first electrically conductive exterior surface is in electrical contact with the first electrically conductive interior surface, or any combination thereof.

Clause 18. The system of any of clauses 15-17, wherein the rotational data includes at least one of the following parameters: a number of times the second electrically conductive exterior surface is in electrical contact with the second electrically conductive interior surface, a duration that the second electrically conductive exterior surface is in electrical contact with the first electrically conductive interior surface, or any combination thereof.

Clause 19. The system of any of clauses 15-18, wherein the axial data includes at least one of the following parameters: an amount of axial displacement of the outer housing relative to the inner housing from the first axial position toward the second axial position, a number of axial displacements of the outer housing relative to the inner housing from the first axial position toward the second axial position, a duration of an axial displacement of the outer housing relative to the inner housing from the first axial position toward the second axial position, or any combination thereof.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

BRIEF DESCRIPTION OF THE DRAWINGS

Additional advantages and details of embodiments or aspects of the present disclosure are explained in greater detail below with reference to the exemplary embodiments that are illustrated in the accompanying schematic figures, in which.

DETAILED DESCRIPTION

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible.

As used herein, the term "computing device" may refer to one or more electronic devices that are configured to directly or indirectly communicate with or over one or more networks. A computing device may be a mobile or portable computing device, a desktop computer, a server, and/or the like. Furthermore, the term "computer" may refer to any computing device that includes the necessary components to receive, process, and output data, and normally includes a display, a processor, a memory, an input device, and a network interface. A "computing system" may include one or more computing devices or computers. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.). Further, multiple computers, e.g., servers, or other computerized devices directly or indirectly communicating in the network environment may constitute a "system" or a "computing system".

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Referring now to FIGS. 1-8, a connector assembly 10 may include an inner housing 100 and an outer housing 200. The inner housing 100 may include a fluid flow path extending between a distal port 102a and a proximal port 102b of the inner housing100. The inner housing 100 may include rails 103 extending in the axial direction of the inner housing 100, an upper opening 105a (e.g., a semi-cylinder or arc shaped opening, etc.) on a first side of the rails 103, and a lower opening 105b (e.g., a semi-cylinder or arc shaped opening, etc.) on a second side of the rails 103 opposite the first side of the rails 103.

An exterior surface 104 of the inner housing 100 may include a first electrically conductive exterior surface 106a and a second electrically conductive exterior surface 106b. The first electrically conductive exterior surface 106a and the second electrically conductive exterior surface 106b may include metallized surfaces formed on the exterior surface 104 of the inner housing 100 by masked vapor deposition, pad printing silver ink, selectively printing and/or molding conductive ribbing, and/or the like. The first electrically conductive exterior surface 106a may surround a circumference of the inner housing 100 adjacent the distal port 102b and/or include one or more extensions extending therefrom toward the proximal port 102a. The second electrically conductive exterior surface 106b may extend along the first side of the rails 103 and/or along a portion of the exterior surface 104 of the inner housing 100 that connects the rails 103 to each other.

In some non-limiting embodiments or aspects, the inner housing 100 may include the BD MaxPlus™ connector, the BD MaxZero™ needle-free connector, and/or the like. However, non-limiting embodiments or aspects are not limited thereto, and the inner housing 100 may include any needleless connector for use in fluid administration.

A first electrical contact 402 may be connected to the exterior surface 104 of the inner housing 100. The first electrical contact 402 may extend from the exterior surface 104 of the inner housing 100 toward the interior surface 204 of the outer housing 200.

The outer housing 200 may surround the inner housing 100. The outer housing 200 may extend between a distal end 202a and a proximal end 202b. The distal end 202a and the proximal end 202b of the outer housing 200 may be located between the distal port 102a and the proximal port 102b of the inner housing 100. An interior surface 204 of the outer housing 200 may include a first electrically conductive interior surface 206a and a second electrically conductive interior surface 206b. The first electrically conductive interior surface 206a and the second electrically conductive exterior surface 206b may include metallized surfaces formed on the interior surface 204 of the outer housing 200 by masked vapor deposition, pad printing silver ink, selectively printing and/or molding conductive ribbing, and/or the like. The first electrically conductive interior surface 206a may surround an opening in the proximal end 202b of the outer housing 200 surrounding the inner housing 100 and face radially inward therefrom and/or include one or more extensions extending therefrom toward the distal end 202a. The second electrically conductive interior surface 206b may be extended on a protrusion(s) 207 that extends radially inward from the interior surface 204 of the outer housing 200 and into the upper opening 105a in the inner housing 100.

The outer housing 200 may include an opening 208 between the distal end 202a and the proximal end 202b, and/or the proximal end 202b of the outer housing 200 may include a groove 210 including a sealing ring 403 configured to form a watertight seal between the distal end 202b of the outer housing 200 and the proximal port 102b of the inner housing 100 (e.g., with the exterior surface 104 of the inner housing 100 at the distal port 102b, etc.). For example, an interior area of the outer housing 200 may be fluidically sealed from an external environment by the inner housing 100 and the outer housing 200.

A printed circuit board assembly (PCBA) 300 may be connected to the interior surface 204 of the outer housing 200. PCBA 300 may include a processor 302 (e.g., a low power microcontroller unit (MCU), etc.), wireless communication circuitry 304, a battery 306, and/or a user input/feedback device 308. PCBA 300 may include an upper surface 310a that faces the interior surface 204 of the inner housing 100 and a lower surface 310b opposite the upper surface 310a and that faces the exterior surface 104 of the inner housing 100. A second electrical contact 404 may be on the lower surface 310b of the PCBA 300 (and/or on the interior surface 204 of the outer housing 200 and electrically connected to the PCBA 300, etc.). The second electrical contact 404 may face the exterior surface 104 of the inner housing 100 including the first electrical contact 402. However, non-limiting embodiments or aspects are not limited thereto, and one or more components of PCBA 300 may be included and/or integrated within inner housing 100 and/or outer housing 200.

PCBA 300 (and/or processor 302) may be electrically connected to and/or electrically interconnect the wireless communication circuitry 304, the battery 306, the user input/feedback device 308, the first electrically conductive interior surface 206a, the second electrically conductive interior surface 206b, and/or the second electrical contact 404.

The wireless communication circuitry 304 may be configured to wirelessly communicate (e.g., via a short range wireless communication connection, such as an NFC communication connection, an RFID communication connection, a Bluetooth® communication connection, and/or the like, etc.) information and/or data with an external computing device. The wireless communication circuitry 304 may be configured to establish communication with an external computing device (e.g., pair and/or activate a pairing sequence for pairing with the external computing device, etc.) based on a predetermined user input to the user input/feedback device 308 (e.g., in response to a user pressing and/or holding the button, etc.).

The battery 306 may include a rechargeable battery, a single use battery, a replaceable battery, or any combination thereof. In some non-limiting embodiments or aspects, the battery 306 may include an energy harvester (e.g., a thermoelectric energy harvester, a photovoltaic energy harvester, a piezoelectric energy harvester, etc.). The battery 306 may provide power for operating components of PCBA 300.

User input/feedback device 308 may be configured to receive a user input from a user and/or to provide feedback to the user. For example, the user input/feedback device 308 may include at least one of the following: a button, a display, a light-emitting diode (LED), an audio output device (e.g., a buzzer, a speaker, etc.), or any combination thereof. The user input/feedback device 308 (e.g., an elastomer button, etc.) may extend through the opening 208 in the outer housing 200 to be visible by and accessible to a user.

A dust cap or shipping wedge 410 may be connected to the distal port 102a of the inner housing 100 and/or the distal end 202a of the outer housing 200. The dust cap or shipping wedge 410 may interrupt a circuit connected to the battery 306 to provide power to the components of the PCBA 300. Removal of the dust cap or shipping wedge 410 may connect (e.g., irreversibility connect, etc.) the components of the PCBA 300 to power from the battery 306.

The outer housing 200 may be configured to move radially relative to the inner housing 100 between a first radial position in which the first electrically conductive exterior surface 106a is spaced apart from the first electrically conductive interior surface 206a and a second radial position in which the first electrically conductive exterior surface 106a is in electrical contact with the first electrically conductive interior surface 206a. For example, and referring specifically to FIG. 5, the first electrically conductive exterior surface 106a and the first electrically conductive interior surface 206a may be brought into and out of contact with each other by a periodic force (e.g., a periodic radial force, etc.) applied to the connector assembly 10 (e.g., radially inward to outer housing 200, radially outward to inner housing 100, etc.), which may open and close a circuit formed by the combination of the first electrically conductive exterior surface 106a and the first electrically conductive interior surface 206a, the opening and closing of which may be detected by processor 302.

The outer housing 200 may be configured to move rotationally relative to the inner housing 100 between a first rotational position in which the second electrically conductive exterior surface 106b is spaced apart from the second electrically conductive interior surface 206b and a second rotational position in which the second electrically conductive exterior surface 106b is in electrical contact with the second electrically conductive interior surface 206b. For example, and referring specifically to FIG. 6, the second electrically conductive exterior surface 106b and the second electrically conductive interior surface 206b may be brought into and out of contact with each other by a periodic force (e.g., a periodic rotational force, etc.) applied to the connector assembly 10 (e.g., rotationally to outer housing 200, rotationally opposite to inner housing 100, etc.), which may open and close a circuit formed by the combination of the second electrically conductive exterior surface 106b and the second electrically conductive interior surface 206b, the opening and closing of which may be detected by processor 302.

Figure 1:
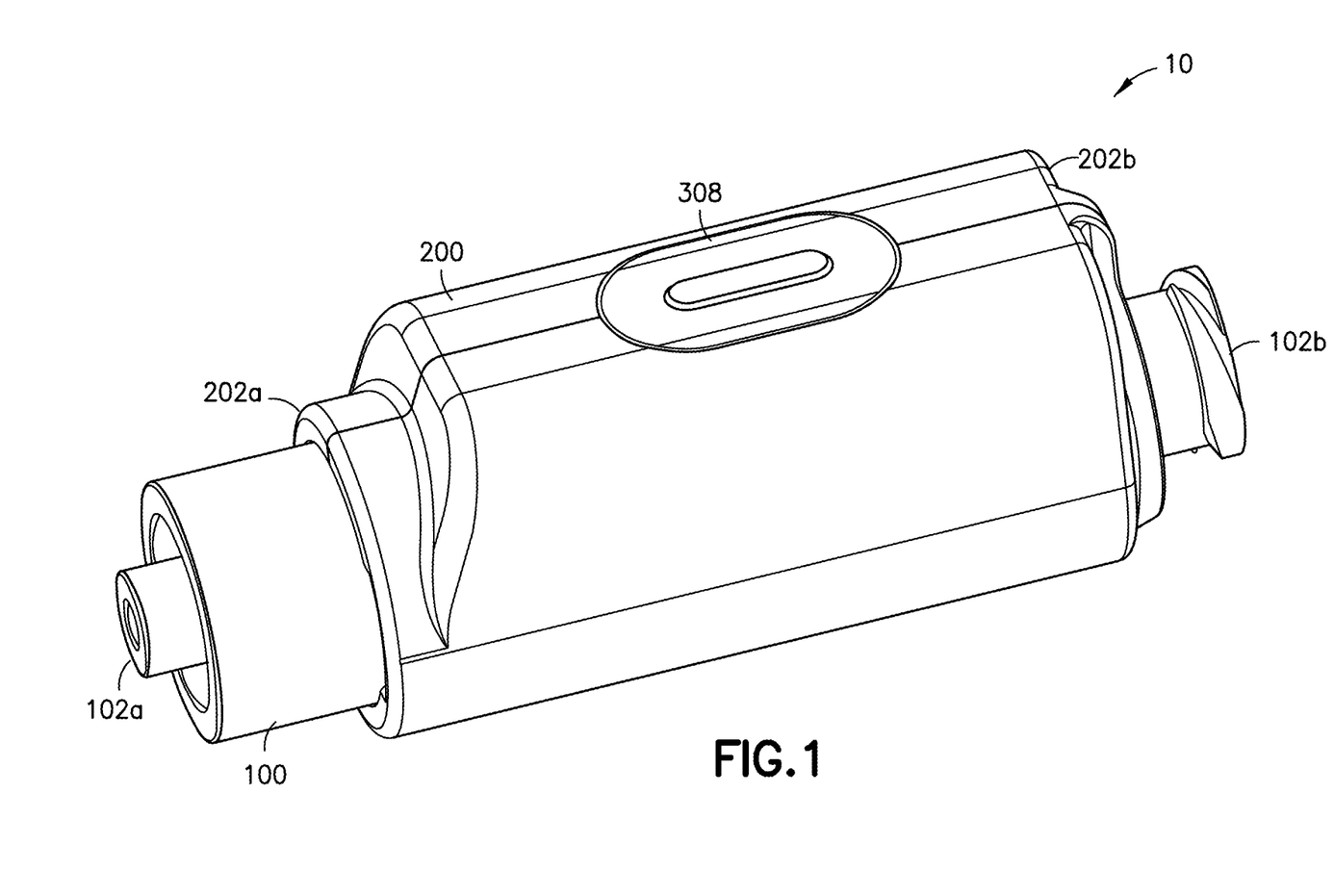
FIG. 1 is a perspective view of non-limiting embodiments or aspects of a connector assembly.
Figure 2:
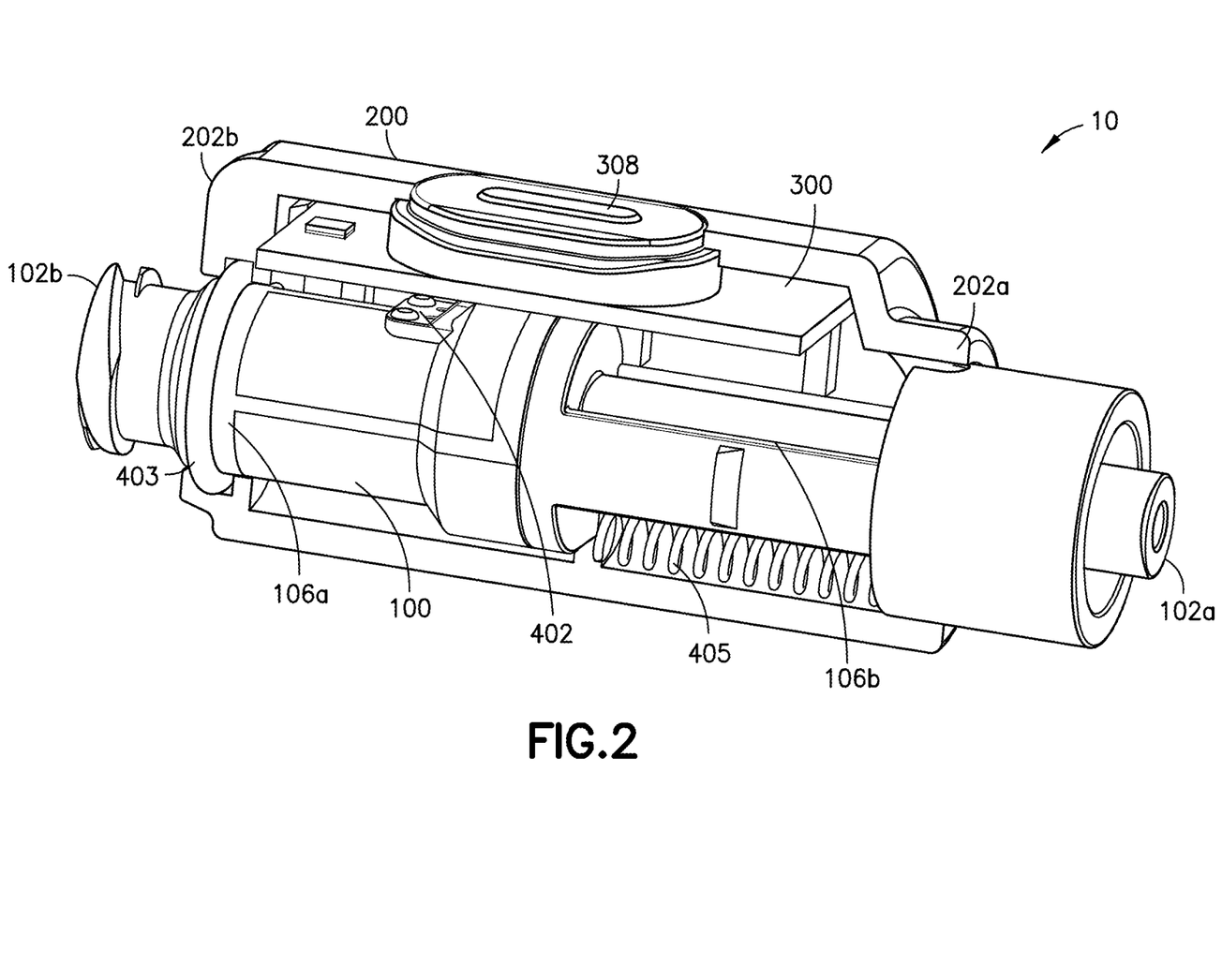
FIG. 2 is a cut-away perspective view of non-limiting embodiments or aspects of a connector assembly.
Figure 3:
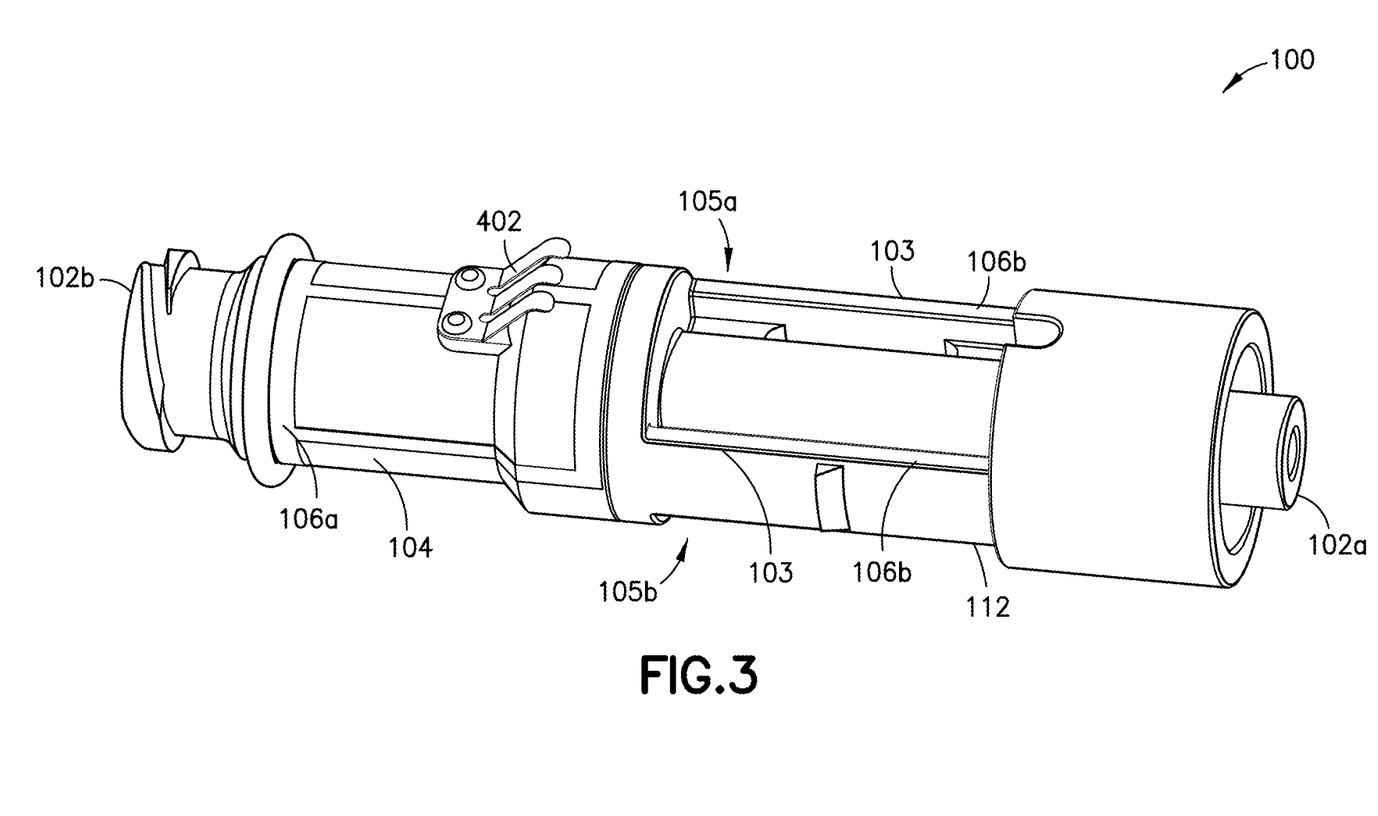
FIG. 3 is a perspective view of non-limiting embodiments or aspects of an inner housing of a connector assembly.
Figure 4:
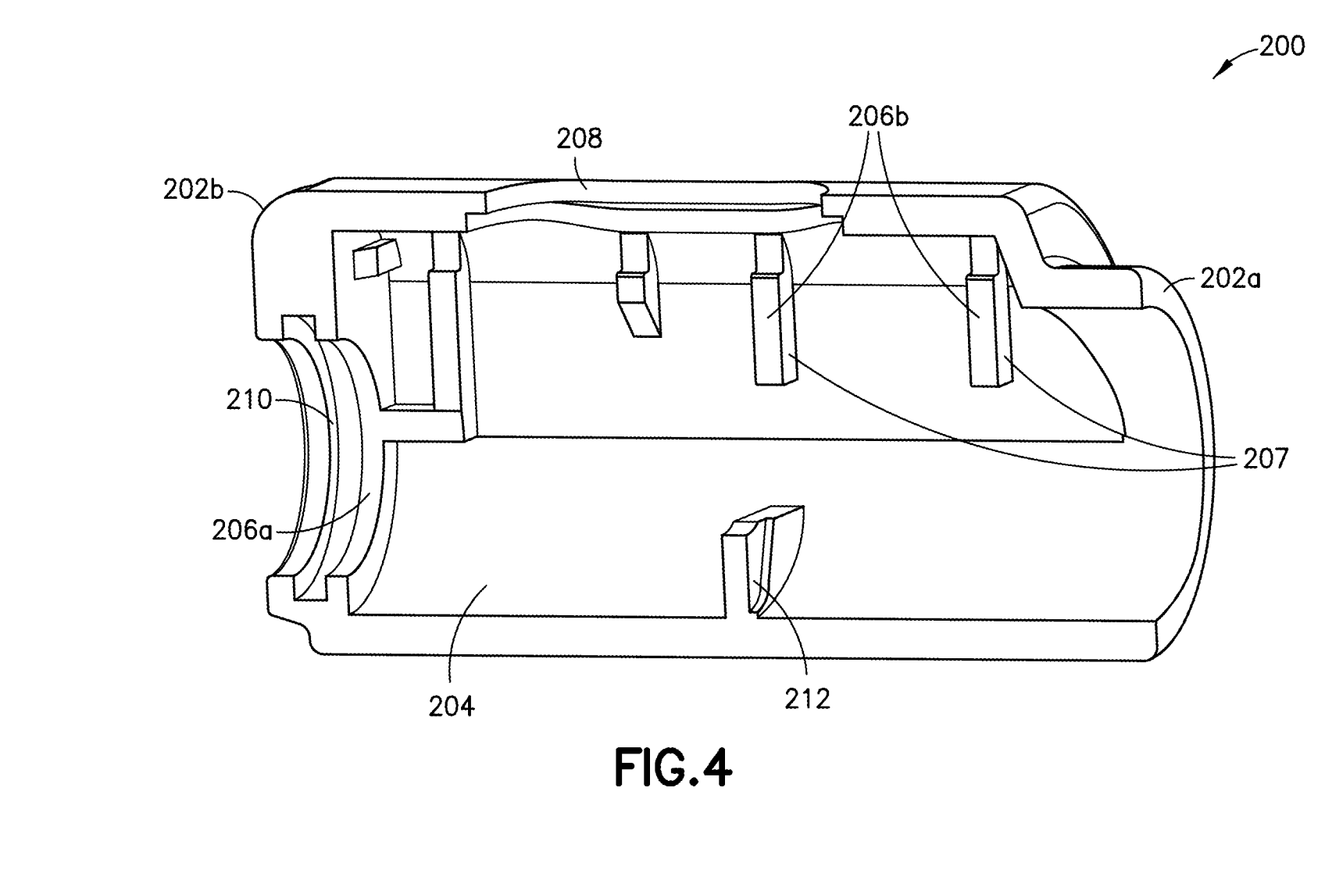
FIG. 4 is a cut-away perspective view of non-limiting embodiments or aspects of an outer housing of a connector assembly.
Figure 5:
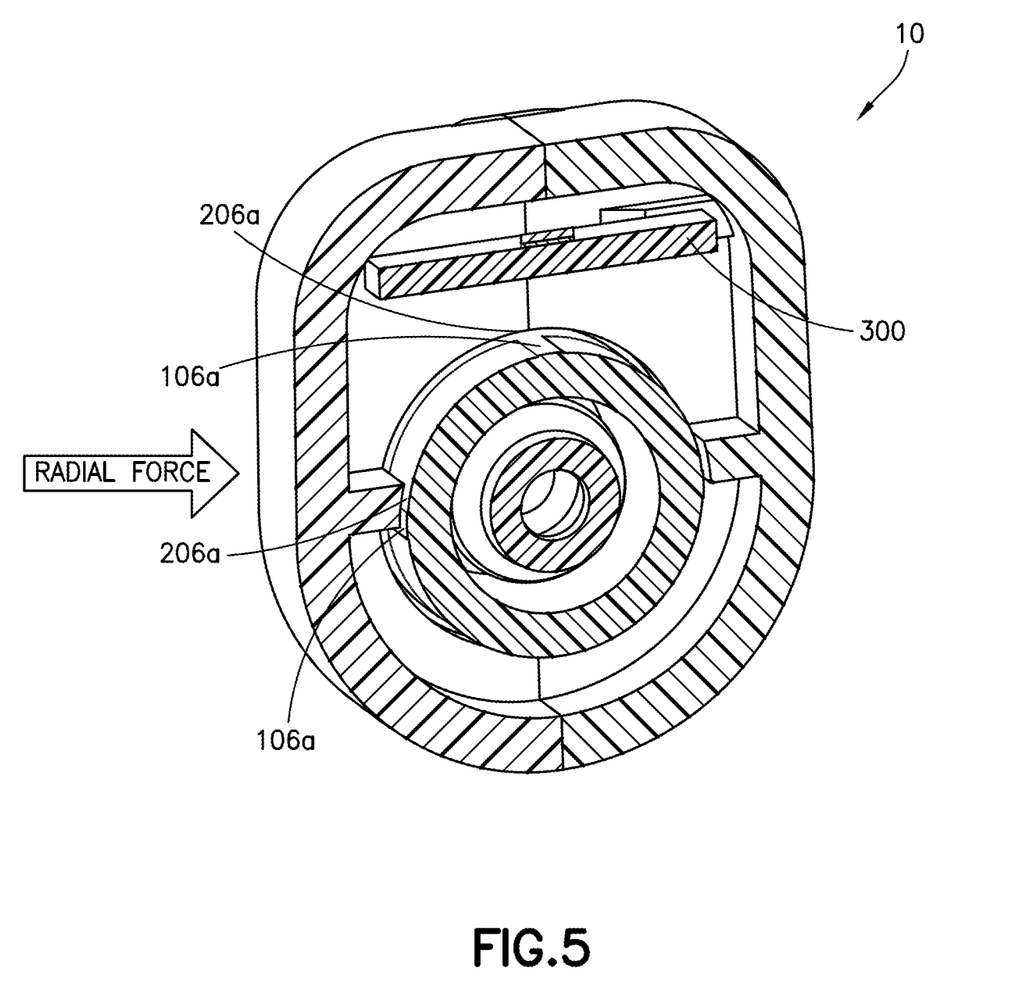
FIG. 5 is a cross-sectional view of non-limiting embodiments or aspects of a connector assembly.
Figure 6:
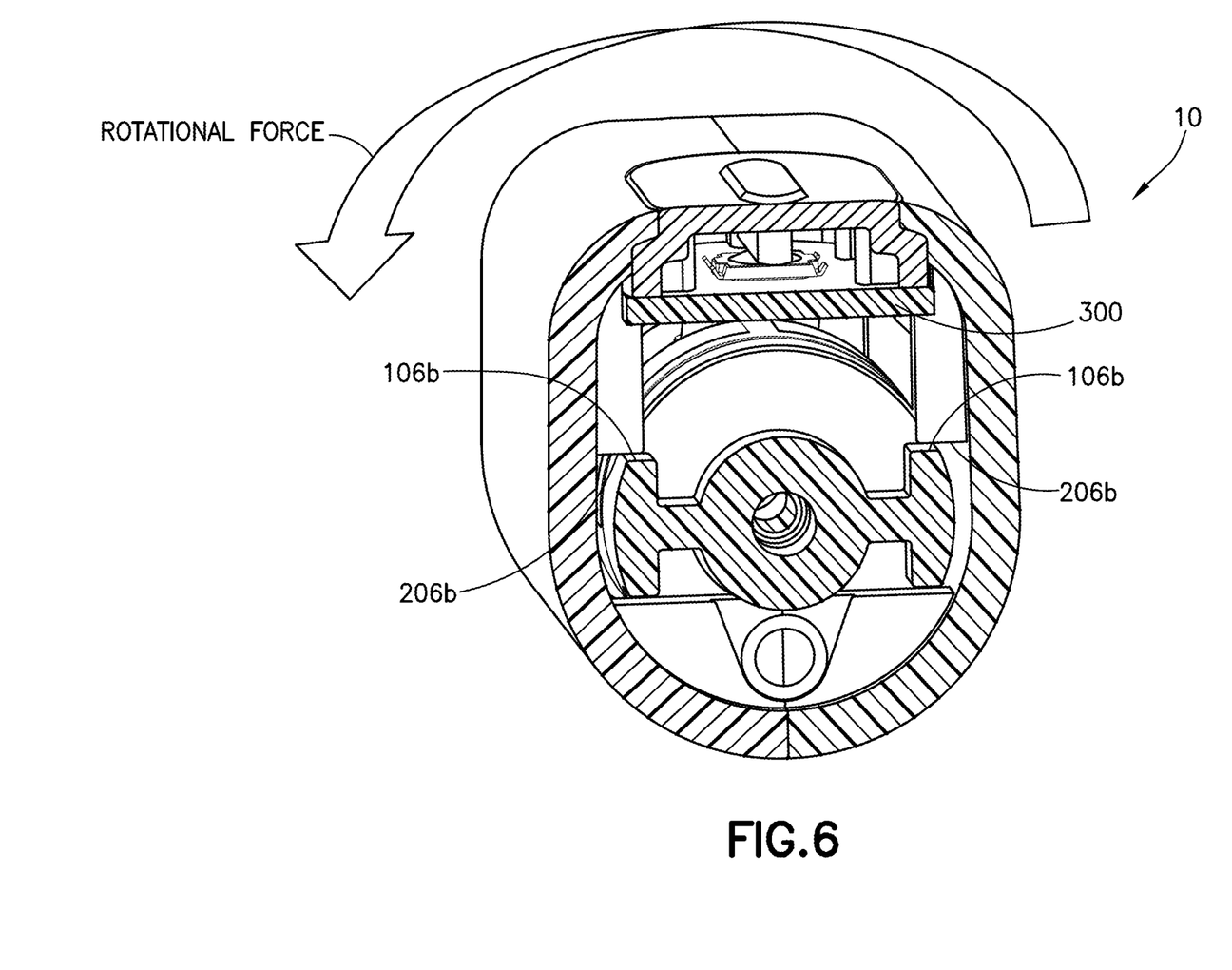
FIG. 6 is another cross-sectional view of non-limiting embodiments or aspects of a connector assembly.
Figure 7:
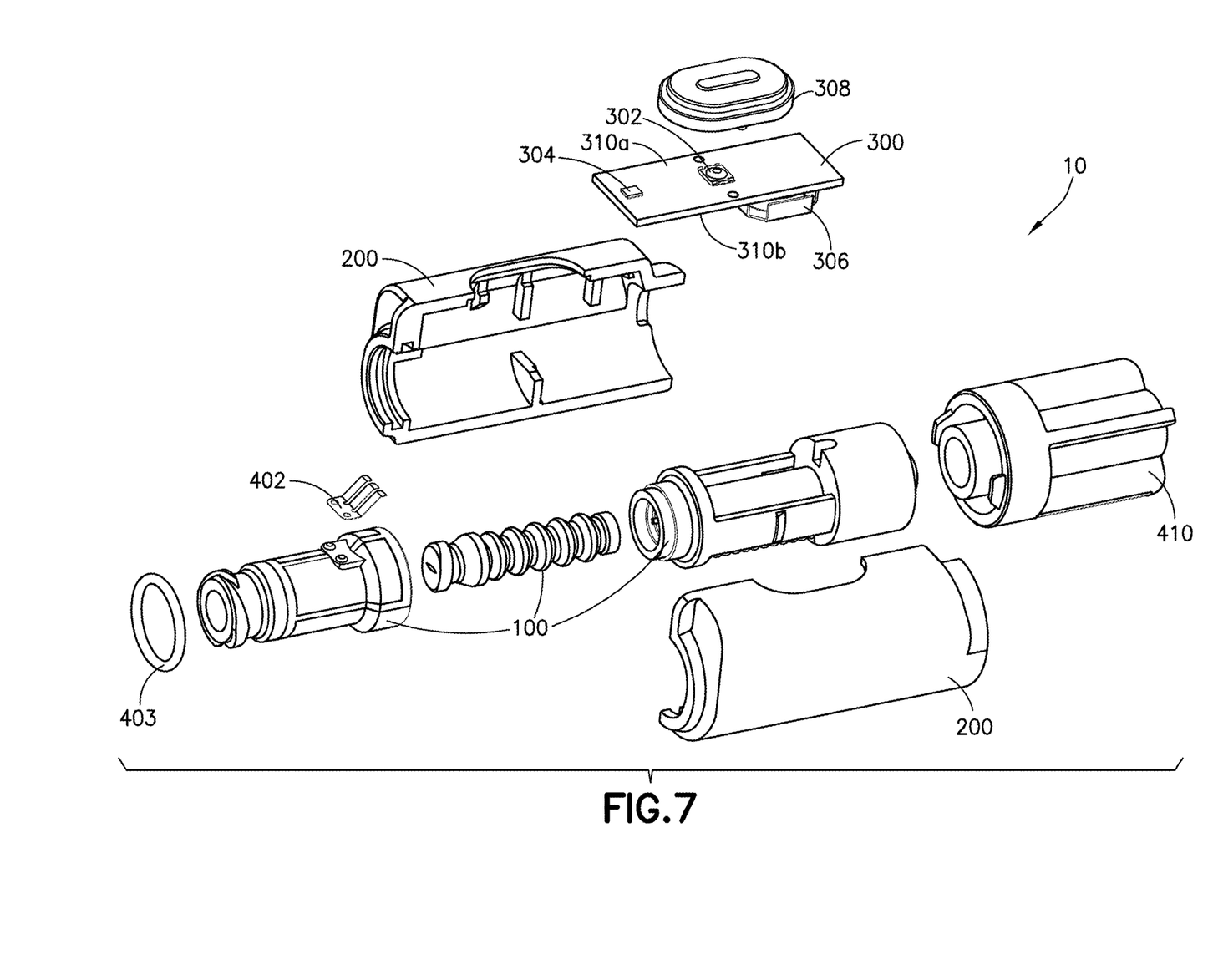
FIG. 7 is an exploded perspective view of non-limiting embodiments or aspects of a connector assembly.
Figure 8:
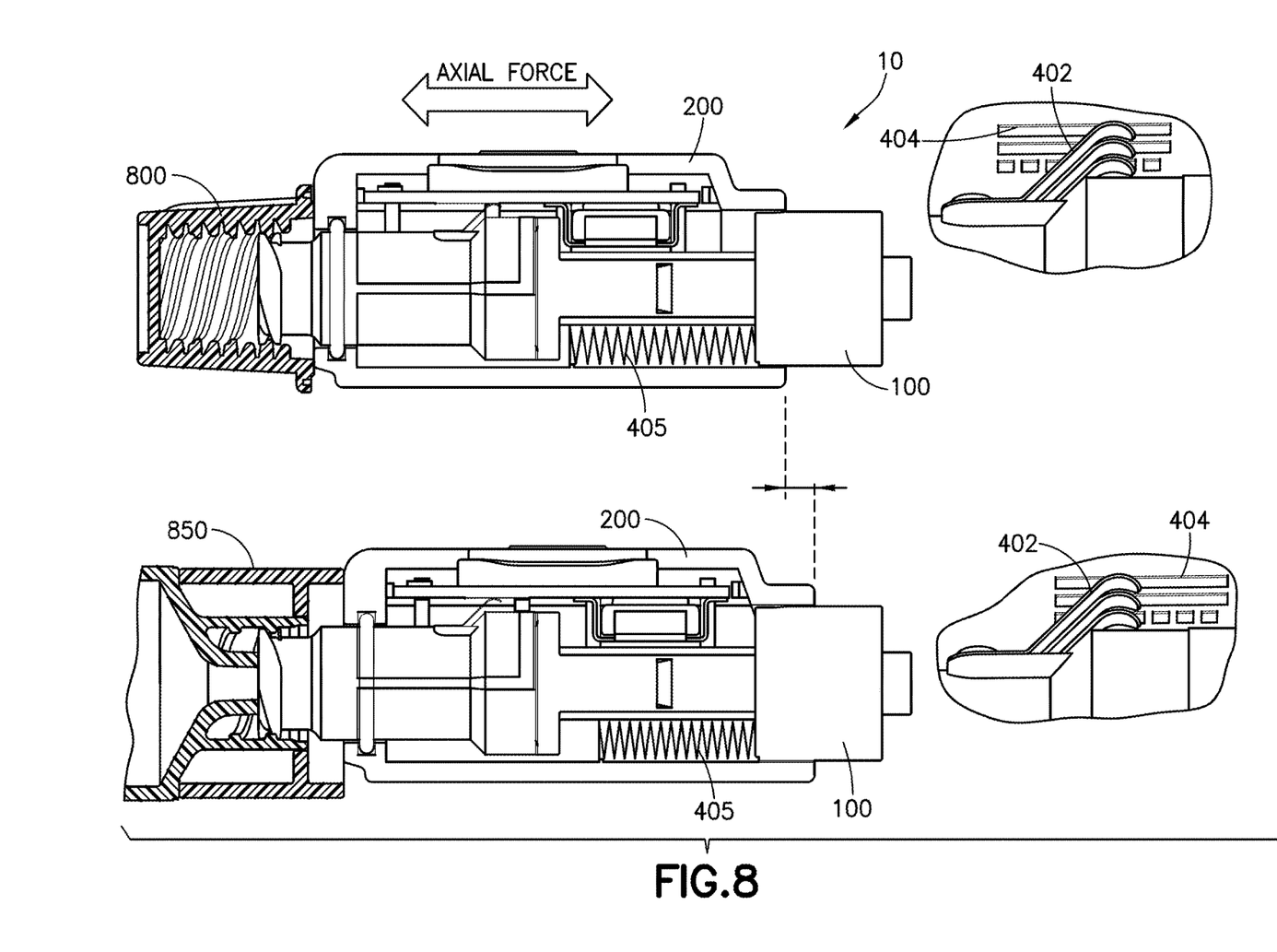
FIG. 8 illustrates non-limiting embodiments or aspects of an axial displacement of an outer housing relative to an inner housing of a connector assembly.

The outer housing 200 may be configured to move axially relative to the inner housing 100 between a first axial position and a second axial position. For example, and referring specifically to FIG. 8, a relative position between the first electrical contact 402 and the second electrical contact 404 may change as the outer housing 200 moves between the first axial position and the second axial position. As an example, one or more characteristics (e.g., a resistance, a voltage, a current, a connection, etc.) of one or more circuits formed by the combination of the first electrical contact 402 and the second electrical contact 404 may change as the outer housing 200 moves between the first axial position and the second axial position, the changing of which may be detected by processor 302. In such an example, the proximal end 202b of the outer housing 200 may make contact with disposable medical devices 800, 850 as they are attached to the proximal port 102b of the inner housing 100, which causes the outer housing 200 to be axially displaced relative to the inner housing 100 by a distance that depends on a geometry of the disposable medical device 800, 850 that is attached. For example, as shown in FIG. 8, disposable medical device 800 causes the outer housing 200 to travel a first distance relative to the inner housing 100 when attached to the distal port 102b, and disposable medical device 850 causes the outer housing 200 to travel a second distance relative to the inner housing 100 when attached to the distal port 102b that is greater than the first distance. As another example, a disposable medical device 800, 850 may create a unique displacement profile when attached to the distal port 102b, such as displacing the outer housing 200 relative to the inner housing 100 a plurality of times to one or more displacement distances before being completely attached at a final displacement distance. The processor 302 may determine the distance traveled or displacement of the outer housing 200 relative to the inner housing 100 based on relative position between the first electrical contact 402 and the second electrical contact 404 as indicated by the one or more characteristics of the one or more circuits formed by the combination of the first electrical contact 402 and the second electrical contact 404.

A spring 405 may be connected between the inner housing 100 and the outer housing 200. For example, the spring 405 may be connected between an end portion 112 of the inner housing 100 within the lower opening 105b in the inner housing 100 and a portion 212 of the outer housing 200 that extends into the lower opening 105b in the inner housing 100 at an opposite end of the lower opening 105b. The spring 405 may be configured to transition between a resting state and a compressed or stretched state. The spring 405 may be configured to be in the resting state when the outer housing 200 is in the first axial position. The spring 405 may be configured to be in the compressed or stretched state when the outer housing 200 is in the second axial position. The spring 405 may cause the outer housing 200 to return to the first axial position in response to a removal of an axial force holding the outer housing 200 in the second axial position. For example, upon removal of a disposal medical device 800,850 attached to the distal port 102b of the inner housing 100, the outer housing 200 may automatically return to the first axial position (e.g., a resting position, etc.), which may indicate to processor 302 that no disposable medical device 800, 850 is attached.

In some non-limiting embodiments or aspects, the second electrical contact 404 may include a plurality of discrete electrical contacts spaced apart from each other, and the first electrical contact 402 (e.g., a sliding/wiping contact, etc.) may be configured to selectively engage the plurality of discrete electrical contacts of the second electrical contact 404 as the outer housing 200 moves axially relative to the inner housing 100 between the first axial position and the second axial position. For example, a plurality of different selective engagements formed by the combination of the first electrical contact 402 and the second electrical contact 404, which may be detected by the processor 302, may be associated with a plurality of different distances or displacements of the outer housing 200 relative to the inner housing 100.

In some non-limiting embodiments or aspects, the second electrical contact 404 may include a continuous resistive element, and the first electrical contact 402 may be configured to engage and move along a length of the continuous resistive element as the outer housing 200 moves axially relative to the inner housing 100 between the first axial position and the second axial position. For example, a plurality of different resistances formed by the combination of the first electrical contact 402 and the second electrical contact 404, which may be detected by the processor 302, may be associated with a plurality of different distances or displacements of the outer housing 200 relative to the inner housing 100 (and/or a plurality of different types of medical devices).

The processor 302 may be programmed and/or configured to determine, based on whether the first electrically conductive exterior surface 106a is in electrical contact with the first electrically conductive interior surface 206a, radial data associated with a radial position of the outer housing 200 relative to the inner housing 100. For example, radial data may include at least one of the following parameters: a number of times that the first electrically conductive exterior surface 106a is in electrical contact with the first electrically conductive interior surface 206a, a duration that the first electrically conductive exterior surface 106a is in electrical contact with the first electrically conductive interior surface 206a, or any combination thereof.

The processor 302 may be programmed and/or configured to determine, based on whether the second electrically conductive exterior surface 106b is in electrical contact with the second electrically conductive interior surface 206b, rotational data associated with a rotational position of the outer housing 200 relative to the inner housing 100. For example, rotational data may include at least one of the following parameters: a number of times the second electrically conductive exterior surface 106b is in electrical contact with the second electrically conductive interior surface 206b, a duration that the second electrically conductive exterior surface 106b is in electrical contact with the first electrically conductive interior surface 206b, or any combination thereof.

The processor 302 may be programmed and/or configured to determine, based on the relative position between the first electrical contact 402 and the second electrical contact 404 (e.g., based on the one or more characteristics of the one or more circuits formed by the combination of the first electrical contact 402 and the second electrical contact 404, etc.), axial data associated with an axial position of the outer housing 200 relative to the inner housing 100. For example, the axial data may include at least one of the following parameters: an amount of axial displacement of the outer housing 200 relative to the inner housing 100 from the first axial position toward the second axial position, a number of axial displacements of the outer housing 200 relative to the inner housing 100 from the first axial position toward the second axial position, a duration of an axial displacement of the outer housing 200 relative to the inner housing 100 from the first axial position toward the second axial position, or any combination thereof.

The wireless communication circuitry 304 may be configured to wirelessly communicate the radial data, the rotational data, and/or the axial data to an external computing device.

The processor 302 (and/or the external computing device) may be programmed and/or configured to determine, based on the radial data and/or the rotational data, a disinfection event associated with the proximal port 102b of the inner housing 100. For example, the processor 302 (and/or the external computing device) may compare the parameters of the radial data and/or the rotational data to one or more thresholds and/or apply one or more algorithms thereto (e.g., one or more machine learning algorithms, etc.) to determine a probability associated with a disinfection event having occurred at the proximal port 102b of the inner housing 100.

The processor 302 (and/or the external computing device) may be programmed and/or configured to determine, based on the axial data, a type of a medical device connected to the distal port 102b of the inner housing 100. For example, the processor 302 (and/or the external computing device) may compare the parameters of the axial data to one or more thresholds and/or apply one or more algorithms thereto (e.g., one or more machine learning algorithms, etc.) to determine a probability associated with a type of a medical device being connected to the distal port 102b of the inner housing 100.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A connector assembly, comprising:
an inner housing including a fluid flow path extending between a proximal port and a distal port, wherein an exterior surface of the inner housing includes a first electrically conductive exterior surface and a second electrically conductive exterior surface;
an outer housing surrounding the inner housing, wherein an interior surface of the outer housing includes a first electrically conductive interior surface and a second electrically conductive interior surface,
wherein the outer housing is configured to move radially relative to the inner housing between a first radial position in which the first electrically conductive exterior surface is spaced apart from the first electrically conductive interior surface and a second radial position in which the first electrically conductive exterior surface is in electrical contact with the first electrically conductive interior surface,
wherein the outer housing is configured to move rotationally relative to the inner housing between a first rotational position in which the second electrically conductive exterior surface is spaced apart from the second electrically conductive interior surface and a second rotational position in which the second electrically conductive exterior surface is in electrical contact with the second electrically conductive interior surface;
at least one processor programmed and/or configured to:
determine, based on whether the first electrically conductive exterior surface is in electrical contact with the first electrically conductive interior surface, radial data associated with a radial position of the outer housing relative to the inner housing; and
determine, based on whether the second electrically conductive exterior surface is in electrical contact with the second electrically conductive interior surface, rotational data associated with a rotational position of the outer housing relative to the inner housing; and
wireless communication circuitry configured to wirelessly communicate the radial data and the rotational data to an external computing device.

2. The connector assembly of claim 1, further comprising:
a first electrical contact connected to the exterior surface of the inner housing;
a second electrical contact connected to the interior surface of the outer housing,
wherein the outer housing is configured to move axially relative to the inner housing between a first axial position and a second axial position,
wherein a relative position between the first electrical contact and the second electrical contact changes as the outer housing moves between the first axial position and the second axial position,
wherein the at least one processor is further programmed and/or configured to determine, based on the relative position between the first electrical contact and the second electrical contact, axial data associated with an axial position of the outer housing relative to the inner housing, and
wherein the wireless communication circuitry is configured to wirelessly communicate the axial data to the external computing device.

3. The connector assembly of claim 2, further comprising:
a spring connected between the inner housing and the outer housing, wherein the spring is configured to transition between a resting state and a compressed or stretched state, wherein the spring is configured to be in the resting state when the outer housing is in the first axial position, wherein the spring is configured to be in the compressed or stretched state when the outer housing is in the second axial position, and wherein the spring causes the outer housing to return to the first axial position in response to a removal of an axial force holding the outer housing in the second axial position.

4. The connector assembly of claim 2, further comprising:
a printed circuit board assembly connected to the interior surface of the outer housing, wherein the printed circuit board assembly includes the at least one processor, the wireless communication circuitry, and the second electrical contact, wherein the printed circuit board assembly is electrically connected to each of the first electrically conductive interior surface and the second electrically conductive interior surface.

5. The connector assembly of claim 4, wherein the second electrical contact includes a plurality of discrete electrical contacts spaced apart from each other, and wherein the first electrical contact is configured to selectively engage the plurality of discrete electrical contacts as the outer housing moves axially relative to the inner housing between the first axial position and the second axial position.

6. The connector assembly of claim 4, wherein the second electrical contact includes a continuous resistive element, wherein the first electrical contact is configured to engage and move along a length of the continuous resistive element as the outer housing moves axially relative to the inner housing between the first axial position and the second axial position.

7. The connector assembly of claim 4, wherein the outer housing extends between a proximal end and a distal end, wherein the proximal end and the distal end of the outer housing are located between the proximal port and the distal port of the inner housing, wherein the printed circuit board assembly further includes a battery and user input device, and wherein the user input device extends through an opening in the outer housing between the proximal end and the distal end of the outer housing.

8. The connector assembly of claim 7, wherein the communication circuitry is configured to establish communication with the external computing device in response to a predetermined user input to the user input device.

9. The connector assembly of claim 7, wherein the connector assembly further includes a sealing ring between the distal end of the outer housing and the distal port of the inner housing.

10. The connector assembly of claim 2, wherein the axial data includes at least one of the following parameters: an amount of axial displacement of the outer housing relative to the inner housing from the first axial position toward the second axial position, a number of axial displacements of the outer housing relative to the inner housing from the first axial position toward the second axial position, a duration of an axial displacement of the outer housing relative to the inner housing from the first axial position toward the second axial position, or any combination thereof.

11. The connector assembly of claim 2, wherein the at least one processor is further programmed and/or configured to determine, based on the axial data, a type of a medical device connected to the distal port of the inner housing.

12. The connector assembly of claim 1, wherein the radial data includes at least one of the following parameters: a number of times that the first electrically conductive exterior surface is in electrical contact with the first electrically conductive interior surface, a duration that the first electrically conductive exterior surface is in electrical contact with the first electrically conductive interior surface, or any combination thereof.

13. The connector assembly of claim 1, wherein the rotational data includes at least one of the following parameters: a number of times the second electrically conductive exterior surface is in electrical contact with the second electrically conductive interior surface, a duration that the second electrically conductive exterior surface is in electrical contact with the first electrically conductive interior surface, or any combination thereof.

14. The connector assembly of claim 1, wherein the at least one processor is further programmed and/or configured to determine, based on the radial data and the rotational data, a disinfection event associated with the distal port of the inner housing.

15. A system, comprising:
a connector assembly including:
an inner housing including a fluid flow path extending between a proximal port and a distal port, wherein an exterior surface of the inner housing includes a first electrically conductive exterior surface and a second electrically conductive exterior surface;
an outer housing surrounding the inner housing, wherein an interior surface of the outer housing includes a first electrically conductive interior surface and a second electrically conductive interior surface,
wherein the outer housing is configured to move radially relative to the inner housing between a first radial position in which the first electrically conductive exterior surface is spaced apart from the first electrically conductive interior surface and a second radial position in which the first electrically conductive exterior surface is in electrical contact with the first electrically conductive interior surface,
wherein the outer housing is configured to move rotationally relative to the inner housing between a first rotational position in which the second electrically conductive exterior surface is spaced apart from the second electrically conductive interior surface and a second rotational position in which the second electrically conductive exterior surface is in electrical contact with the second electrically conductive interior surface;
at least one processor programmed and/or configured to:
determine, based on whether the first electrically conductive exterior surface is in electrical contact with the first electrically conductive interior surface, radial data associated with a radial position of the outer housing relative to the inner housing; and
determine, based on whether the second electrically conductive exterior surface is in electrical contact with the second electrically conductive interior surface, rotational data associated with a rotational position of the outer housing relative to the inner housing; and wireless communication circuitry configured to wirelessly communicate the radial data and the rotational data to an external computing device; and a computing system including one or more processors programmed and/or configured to determine, based on the radial data and the rotational data, a disinfection event associated with the distal port of the inner housing.

16. The system of claim 15, wherein the connector assembly further includes:
a first electrical contact connected to the exterior surface of the inner housing;
a second electrical contact connected to the interior surface of the outer housing,
wherein the outer housing is configured to move axially relative to the inner housing between a first axial position and a second axial position,
wherein a relative position between the first electrical contact and the second electrical contact changes as the outer housing moves between the first axial position and the second axial position,
wherein the at least one processor is further programmed and/or configured to determine, based on the relative position between the first electrical contact and the second electrical contact, axial data associated with an axial position of the outer housing relative to the inner housing,
wherein the wireless communication circuitry is configured to wirelessly communicate the axial data to the external computing device,
and wherein the one or more processors are further programmed and/or configured to determine, based on the axial data, a type of a medical device connected to the distal port of the inner housing.

17. The system of claim 16, wherein the axial data includes at least one of the following parameters: an amount of axial displacement of the outer housing relative to the inner housing from the first axial position toward the second axial position, a number of axial displacements of the outer housing relative to the inner housing from the first axial position toward the second axial position, a duration of an axial displacement of the outer housing relative to the inner housing from the first axial position toward the second axial position, or any combination thereof.

18. The system of claim 15, wherein the radial data includes at least one of the following parameters: a number of times that the first electrically conductive exterior surface is in electrical contact with the first electrically conductive interior surface, a duration that the first electrically conductive exterior surface is in electrical contact with the first electrically conductive interior surface, or any combination thereof.

19. The system of claim 15, wherein the rotational data includes at least one of the following parameters: a number of times the second electrically conductive exterior surface is in electrical contact with the second electrically conductive interior surface, a duration that the second electrically conductive exterior surface is in electrical contact with the first electrically conductive interior surface, or any combination thereof.

* * * * *